United States Patent
Esteves et al.

(10) Patent No.: US 12,077,562 B2
(45) Date of Patent: Sep. 3, 2024

(54) AAV CAPSIDS IDENTIFIED BY IN VIVO LIBRARY SELECTION

(71) Applicants: University of Massachusetts, Boston, MA (US); The Johns Hopkins University, Baltimore, MD (US); Kennedy Krieger Institute, Inc., Baltimore, MD (US)

(72) Inventors: Miguel Sena Esteves, Westford, MA (US); Sourav Roy Choudhury, Newton, MA (US); Kathryn Rae Wagner, Baltimore, MD (US); Jennifer Gifford Green, Chelmsford, MA (US); Ana Rita Batista, West Boylston, MA (US)

(73) Assignees: University of Massachusetts, Boston, MA (US); The Johns Hopkins University, Baltimore, MD (US); Kennedy Krieger Institute, Inc., Baltimore, MD (US)

( * ) Notice: Subject to any disclaimer, the term of this patent is extended or adjusted under 35 U.S.C. 154(b) by 46 days.

(21) Appl. No.: 17/930,166

(22) Filed: Sep. 7, 2022

(65) Prior Publication Data

US 2023/0067741 A1 Mar. 2, 2023

Related U.S. Application Data

(63) Continuation of application No. 17/050,475, filed as application No. PCT/US2019/029489 on Apr. 26, 2019, now Pat. No. 11,472,848.

(60) Provisional application No. 62/663,988, filed on Apr. 27, 2018.

(51) Int. Cl.
| | |
|---|---|
| *C07K 14/01* | (2006.01) |
| *C07K 14/005* | (2006.01) |
| *C07K 14/015* | (2006.01) |
| *C07K 14/47* | (2006.01) |
| *C12N 7/00* | (2006.01) |
| *A61K 38/00* | (2006.01) |

(52) U.S. Cl.
CPC .............. *C07K 14/01* (2013.01); *C12N 7/00* (2013.01); *A61K 38/00* (2013.01); *C12N 2310/141* (2013.01); *C12N 2750/14122* (2013.01)

(58) Field of Classification Search
CPC ...... A61K 38/00; C07K 14/005; C07K 14/01; C12N 2310/141; C12N 2750/14122
See application file for complete search history.

(56) References Cited

U.S. PATENT DOCUMENTS

| | | |
|---|---|---|
| 11,472,848 B2 | 10/2022 | Esteves et al. |
| 2021/0238233 A1 | 8/2021 | Esteves et al. |

FOREIGN PATENT DOCUMENTS

| | | |
|---|---|---|
| WO | WO 2009/137006 A2 | 11/2009 |
| WO | WO 2016/054554 A1 | 4/2016 |

OTHER PUBLICATIONS

Extended European Search Report for Application No. 19791807.1, mailed Feb. 23, 2022.
Invitation to Pay Additional Fees for Application No. PCT/US2019/029489, mailed Jul. 15, 2019.
International Search Report and Written Opinion for Application No. PCT/US2019/029489, mailed Sep. 10, 2019.
International Preliminary Report on Patentability for Application No. PCT/US2019/029489, mailed Nov. 5, 2020.
No Author Listed, Database Geneseq Accession No. AXS19983. Adeno-associated virus mosaic (MM19) capsid gene, SEQ ID 105. First entry: Dec. 24, 2009, Revised: Sep. 30, 2010. 2 pages.
No Author Listed, Database Geneseq Accession No. AXS19892. Adeno-associated virus mosaic (M67) capsid protein, SEQ ID 14. First entry: Dec. 24, 2009. 1 page.
Choudhury et al., In Vivo Selection Yields AAV-B1 Capsid for Central Nervous System and Muscle Gene Therapy. Mol Ther. Aug. 2016;24(7):1247-57. doi: 10.1038/mt.2016.84. Epub Apr. 27, 2016.
Dufour et al., Intrajugular vein delivery of AAV9-RNAi prevents neuropathological changes and weight loss in Huntington's disease mice. Mol Ther. Apr. 2014;22(4):797-810. doi: 10.1038/mt.2013.289. Epub Jan. 6, 2014.
Foust et al., Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Foust et al., Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010.
Foust et al., Therapeutic AAV9-mediated suppression of mutant SOD1 slows disease progression and extends survival in models of inherited ALS. Mol Ther. Dec. 2013;21(12):2148-59. doi: 10.1038/mt.2013.211. Epub Sep. 6, 2013.
Fu et al., Correction of neurological disease of mucopolysaccharidosis IIIB in adult mice by rAAV9 trans-blood-brain barrier gene delivery. Mol Ther. Jun. 2011;19(6):1025-33. doi: 10.1038/mt.2011.34. Epub Mar. 8, 2011.
Fu et al., Significantly increased lifespan and improved behavioral performances by rAAV gene delivery in adult mucopolysaccharidosis IIIB mice. Gene Ther. Jul. 2007;14(14):1065-77. doi: 10.1038/sj.gt.3302961. Epub Apr. 26, 2007.

(Continued)

*Primary Examiner* — Barry A Chestnut
(74) *Attorney, Agent, or Firm* — Wolf, Greenfield & Sacks, P.C.

(57) ABSTRACT

The disclosure relates, in some aspects, to adeno-associated virus capsid proteins isolated from an in vivo library and recombinant adeno-associated viruses (rAAVs) comprising the same. In some aspects, the disclosure relates to isolated nucleic acids encoding AAV capsid proteins isolated from an in vivo library. In some embodiments, rAAVs and compositions described by the disclosure are useful for delivery of one or more transgenes to the muscle-tissue of a subject.

11 Claims, 2 Drawing Sheets

Specification includes a Sequence Listing.

(56) References Cited

OTHER PUBLICATIONS

Kotterman et al., Engineering adeno-associated viruses for clinical gene therapy. Nat Rev Genet. Jul. 2014;15(7):445-51. doi: 10.1038/nrg3742. Epub May 20, 2014.

McCarty et al., Mannitol-facilitated CNS entry of rAAV2 vector significantly delayed the neurological disease progression in MPS IIIB mice. Gene Ther. Nov. 2009;16(11):1340-52. doi: 10.1038/gt.2009.85. Epub Jul. 9, 2009.

Meng et al., Effective intravenous therapy for neurodegenerative disease with a therapeutic enzyme and a peptide that mediates delivery to the brain. Mol Ther. Mar. 2014;22(3):547-553. doi: 10.1038/mt.2013.267. Epub Dec. 26, 2013.

Ruzo et al., Correction of pathological accumulation of glycosaminoglycans in central nervous system and peripheral tissues of MPSIIIA mice through systemic AAV9 gene transfer. Hum Gene Ther. Dec. 2012;23(12):1237-46. doi: 10.1089/hum.2012.029. Epub Oct. 17, 2012.

Sarkar et al., A carrier for non-covalent delivery of functional beta-galactosidase and antibodies against amyloid plaques and IgM to the brain. PLoS One. 2011;6(12):e28881. doi: 10.1371/journal.pone.0028881. Epub Dec. 21, 2011.

Sarkar et al., Peptide carrier-mediated non-covalent delivery of unmodified cisplatin, methotrexate and other agents via intravenous route to the brain. PLoS One. May 21, 2014;9(5):e97655. doi: 10.1371/journal.pone.0097655.

Thévenot et al., Targeted delivery of self-complementary adeno-associated virus serotype 9 to the brain, using magnetic resonance imaging-guided focused ultrasound. Hum Gene Ther. Nov. 2012;23(11):1144-55. doi: 10.1089/hum.2012.013. Epub Oct. 15, 2012.

Weber-Adrian et al., Gene delivery to the spinal cord using MRI-guided focused ultrasound. Gene Ther. Jul. 2015;22(7):568-77. doi: 10.1038/gt.2015.25. Epub Apr. 23, 2015.

Yang et al., Global CNS transduction of adult mice by intravenously delivered rAAVrh.8 and rAAVrh.10 and nonhuman primates by rAAVrh.10. Mol Ther. Jul. 2014;22(7):1299-1309. doi: 10.1038/mt.2014.68. Epub Apr. 30, 2014.

Zhang et al., Several rAAV vectors efficiently cross the blood-brain barrier and transduce neurons and astrocytes in the neonatal mouse central nervous system. Mol Ther. Aug. 2011;19(8):1440-8. doi: 10.1038/mt.2011.98. Epub May 24, 2011.

SEQUENCE LISTING

```
Sequence total quantity: 7
SEQ ID NO: 1              moltype = DNA   length = 2214
FEATURE                   Location/Qualifiers
misc_feature              1..2214
                          note = Synthetic polynucleotide
source                    1..2214
                          mol_type = other DNA
```

```
                organism = synthetic construct
SEQUENCE: 1
atggctgccg atggttatct tccagattgg ctcgaggaca acctctctga gggcattcgc    60
gagtggtggg cgctgaaacc tggagccccg aagcccaaag ccaaccagca aaagcaggac   120
gacggccggg gtctggtgct tcctggctac aagtacctcg gacccttcaa cggactcgac   180
aaggggagc ccgtcaacgc ggcggacgca gcggccctcg agcacgacaa ggcctacgac    240
cagcagctgc aggcgggtga caatccgtac ctgcggtata accacgccga cgccgagttt   300
caggagcgtc tgcaagaaga tacgtctttt ggggcaacc tcgggcgagc agtcttccag    360
gccaagaagc gggttctcga acctctcggt ctggttgagg aaggcgctaa gacggctcct   420
ggaaagaaga gaccagtaga gcagtcaccc caagaaccag actcctcctc gggcatcggc   480
aagaaaggcc aacagcccgc cagaaaaaga ctcaattttg gtcagactgg cgactcagag   540
tcagtccccg atccacaacc tctcggagaa cctccagcag cccctcagg tctgggacct    600
aatacaatgg cttcaggcgg tggcgctcca atggcagaca taacgaagg cgccgacgga    660
gtgggtaatt cctcgggaaa ttggcattgc gattccanat ggctgggcga cagagtcatc   720
accaccagca cccgaacctg ggccctgccc acctacaaca accacctcta caagcaaata   780
tccaatggga catcgggagg aagcaccaac gacaacacct acttcggcta cagcaccccc   840
tgggggtatt ttgacttcaa cagattccac tgccactttt caccacgtga ctggcagcga   900
ctcatcaaca acaactgggg attccggccc aagagactca gcttcaagct cttcaacatc   960
caggtcaagg aggtcacgca gaatgatggc gtcacaacca tcgctaataa ccttaccagc  1020
acggttcaag tcttctcgga ctcggagtac cagcttccgt acgtcctcgg ctctgcgcac  1080
cagggctgcc tccctccgtt cccggcgga cgtgttcatga ttccgcaata cggctacctg  1140
acgctcaaca atggcagcca agccgtggga cgttcatcct tttactgcct ggaatatttc  1200
ccatcgcaga tgctgagaac gggcaataac tttaccttca gctacacctt cgaggacgtg  1260
ccttttccaca gcagctacgc gcacagccag agcctggacc ggctgatgaa tcctctcatc  1320
gaccagtacc tgtattacct gaacagaact cagaatcagt ccggaagtgc ccaaaacaag  1380
gacttgctgt ttagccgggg gtctccagct ggcatgtctg ttcagcccaa aaactggcta  1440
cctggaccct gttatcggca gcagcgcgtt tctaaaacaa aaacagacaa caacaacagc  1500
aatttttacct ggactggtgc ttcaaaatat aaacctcaatg ggcgtgaatc catcatcaac  1560
cctggcactg ctatggcctc acacaaagac gacgaagaca agttctttcc catgagtggt  1620
gtcatgattt ttggaaaaga gagcgccgga gcttcaaacc ctgcattgga caatgtcatc  1680
attacagacg aagaggaaat taaagccact aaccctgtgg ccaccgaaag atttgggacc  1740
gtggcagtca atttccagag cagcagcaca gaccctgcga ccggagatgt gcatgttatg  1800
ggagccttac ctgaatggt gtggcaagac agagacgtat acctgcaggg tcctatttgg  1860
gccaaaattc ctcacacgga tggacacttt caccgtctc tctctcatgg cggctttgga  1920
cttaagcacc cgcctcctca gatcctcatc aaaaacacgc ctgttcctgc gaatcctccg  1980
gcagagtttt cggctacaaa gtttgcttca ttcatcaccc agtattccac aggacaagtg  2040
agcgtggaga ttgaatggga gctgcagaaa gaaaacagca aacgctgaa tcccgaagtg  2100
cagtatacat ctaactatgc aaaatctgcc aacgttgatt tcactgtgga caacaatgga  2160
ctttatactg agcctcgccc cattggcacc cgttacctca cccgtcccct gtaa         2214

SEQ ID NO: 2           moltype = DNA   length = 2214
FEATURE                Location/Qualifiers
misc_feature           1..2214
                       note = Synthetic polynucleotide
source                 1..2214
                       mol_type = other DNA
                       organism = synthetic construct
SEQUENCE: 2
atggctgccg atggttatct tccagattgg ctcgaggaca acctctctga gggcattcgc    60
gagtggtggg acctgaaacc tggagccccc aagcccaagg ccaaccagca gaagcaggac   120
gacggccggg gtctggtgct tcctggctac aagtacctcg gacccttcaa cggactcgac   180
aaggggagc ccgtcaacgc ggcggacgca gcggccctcg agcacgacaa ggcctacgac    240
cagcagctgc aggcgggtga caatccgtac ctgcggtata accacgccga cgccgagttt   300
caggagcgtc tgcaagaaga tacgtctttt ggggcaacc tcgggagagc agtcttccag    360
gccaagaagc gggttctcga acctctcggt ctggttgagg aaggcgctaa gacggctcct   420
ggaaagaaga gaccggtaga gccatcaccc cagcgttctc cagactcctc tacgggcatc   480
ggcaaaaaag gccaacagcc cgccagaaaa agactcaatt ttggcagac tggcgactca   540
gagtcagttc cagaccctca acctctcgga gaacctccag cagcgcctc tggtgtggga   600
cctaatacaa tggctgcagg cggtgcgca ccaatgcgaca acataacgaag agcgccgac   660
ggagtgggta gttcctcggg aaattggcat tgcgattcca catggctggg cgacagagtc   720
atcaccacca gcacccgcac ctgggccttg cccacctaca ataaccacct ctacaagcaa   780
atctccagtg cttcaacggg ggccagcaac gacaacacct acttcggcta cagcaccccc   840
tgggggtatt ttgactttaa cagattccac tgccactttt caccacgtga ctggcagcga   900
ctcatcaaca acaactgggg attccggccc aagagactca gcttcaagct cttcaacatc   960
caggtcaagg aggtcacgca gaatgaaggc accaagacca tcgccaataa cctcaccagc  1020
accatccagg tgtttacgga ctcggagtac cagctgccgt acgttctcgg ctctgcccac  1080
cagggctgcc tgcctccgtt cccggcgga cgtgttcatga ttcccagta cggctaccta   1140
acactcaaca acggtagtca ggccgtggga cgctcctcct ctactgcct ggaatactttt  1200
ccttcgcaga tgctgagaac gggcaacaac tttgagttca gctaccagtt tgaggacgtg  1260
ccttttcaca gcagctacgc gcacagccaa agcctggacc ggctgatgaa ccctctgatt  1320
gaccagtacc tgtactactt gtctcggact caaacaacag gaggcacggc aaatacgcag  1380
actctgggct tcagccaagg tgggcctaat acaatggcca atcaggcaaa gaactggctg  1440
ccaggaccct gttaccgcca caacgcgtc tcaacgacaa ccgggcaaaa caacaatagc  1500
aactttgcct ggactgctgg gaccaaatac catctgaatg gaagaaattc attggctaat  1560
cctggcatcg ctatggcaac acacaaagac gacgaggagc gttttttttcc cagtaacggg  1620
atcctgattt ttggcaaaca aaatgctgcc agagacaatg cggattacag cgatgtcatg  1680
ctcaccagca ggaagaaat caaaaccact aaccctgtgg ctacagagga atacggtatc  1740
gtggcagata cttgcagca gcaaaacacg gctcctcaaa ttggaactgt caacagccag  1800
ggggccttac ccggtatggt ctggcaggac agagatgtgt accttcaggg gcccatctgg  1860
```

```
gcaaagattc cacacacgga cggcaacttc cacccgtctc cgctgatggg cggctttggc  1920
ctgaaacatc ctccgcctca gatcctgatc aagaacacgc ctgtacctgc ggatcctccg  1980
accaccttca accagtcaaa gtttgcttca ttcatcaccc aatactccac aggacaagtg  2040
agtgtgaaa ttgaatggga gctgcagaaa gaaaacagca agcgctggaa tcccgaagtg  2100
cagtacacat ccaattatgc aaaatctgcc aacgttgatt ttactgtgga caacaatgga  2160
ctttatactg agcctcgccc cattggcacc cgttaccta cccgtccct gtaa          2214
```

```
SEQ ID NO: 3              moltype = AA   length = 736
FEATURE                   Location/Qualifiers
REGION                    1..736
                          note = Synthetic polypeptide
source                    1..736
                          mol_type = protein
                          organism = synthetic construct
SEQUENCE: 3
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                  736
```

```
SEQ ID NO: 4              moltype = AA   length = 736
FEATURE                   Location/Qualifiers
REGION                    1..736
                          note = Synthetic polypeptide
source                    1..736
                          mol_type = protein
                          organism = synthetic construct
SEQUENCE: 4
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPFG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD KDKFFPMSGV  540
MIFGKESAGA SNTALDNVMI TDEEEIKATN PVATERFGTV AVNLQSSSTD PATGDVHVMG  600
ALPGMVWQDR DVYLQGPIWA KIPHTDGHFH PSPLMGGFGL KHPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                  736
```

```
SEQ ID NO: 5              moltype = AA   length = 738
FEATURE                   Location/Qualifiers
REGION                    1..738
                          note = Synthetic polypeptide
source                    1..738
                          mol_type = protein
                          organism = synthetic construct
SEQUENCE: 5
MAADGYLPDW LEDNLSEGIR EWWALKPGAP KPKANQQKQD DGRGLVLPGY KYLGPFNGLD   60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                738
```

```
SEQ ID NO: 6              moltype = AA   length = 737
FEATURE                   Location/Qualifiers
REGION                    1..737
                          note = Synthetic polypeptide
source                    1..737
                          mol_type = protein
```

```
                    organism = synthetic construct
SEQUENCE: 6
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEQSP QEPDSSSGIG KKGQQPARKR LNFGQTGDSE    180
SVPDPQPLGE PPAAPSGLGP NTMASGGGAP MADNNEGADG VGNSSGNWHC DSTWLGDRVI    240
TTSTRTWALP TYNNHLYKQI SNGTSGGSTN DNTYFGYSTP WGYFDFNRFH CHFSPRDWQR    300
LINNNWGFRP KRLSFKLFNI QVKEVTQNDG VTTIANNLTS TVQVFSDSEY QLPYVLGSAH    360
QGCLPPFPAD VFMIPQYGYL TLNNGSQAVG RSSFYCLEYF PSQMLRTGNN FTFSYTFEDV    420
PFHSSYAHSQ SLDRLMNPLI DQYLYYLNRT QNQSGSAQNK DLLFSRGSPA GMSVQPKNWL    480
PGPCYRQQRV SKTKTDNNNS NFTWTGASKY NLNGRESIIN PGTAMASHKD DEDKFFPMSG    540
VMIFGKESAG ASNTALDNVM ITDEEEIKAT NPVATERFGT VAVNFQSSST DPATGDVHVM    600
GALPGMVWQD RDVYLQGPIW AKIPHTDGHF HPSPLMGGFG LKHPPPQILI KNTPVPANPP    660
AEFSATKFAS FITQYSTGQV SVEIEWELQK ENSKRWNPEV QYTSNYAKSA NVDFTVDNNG    720
LYTEPRPIGT RYLTRPL                                                  737

SEQ ID NO: 7         moltype = AA  length = 737
FEATURE              Location/Qualifiers
REGION               1..737
                     note = Synthetic polypeptide
source               1..737
                     mol_type = protein
                     organism = synthetic construct
SEQUENCE: 7
MAADGYLPDW LEDNLSEGIR EWWDLKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEXAD GVGSSSGNWH CDSTWLGDRV    240
ITTSTRTWAL PTYNNHLYKQ ISSASTGASN DNTYFGYSTP WGYFDFNRFH CHFSPRDWQR    300
LINNNWGFRP KRLSFKLFNI QVKEVTQNEG TKTIANNLTS TIQVFTDSEY QLPYVLGSAH    360
QGCLPPFPAD VFMIPQYGYL TLNNGSQAVG RSSFYCLEYF PSQMLRTGNN FEFSYQFEDV    420
PFHSSYAHSQ SLDRLMNPLI DQYLYYLSRT QTTGGTANTQ TLGFSQGGPN TMANQAKNWL    480
PGPCYRQQRV STTTGQNNNS NFAWTAGTKY HLNGRNSLAN PGIAMATHKD DEERFFPSNG    540
ILIFGKQNAA RDNADYSDVM LTSEEEIKTT NPVATEEYGI VADNLQQQNT APQIGTVNSQ    600
GALPGMVWQD RDVYLQGPIW AKIPHTDGNF HPSPLMGGFG LKHPPPQILI KNTPVPADPP    660
TTFNQSKFAS FITQYSTGQV SVEIEWELQK ENSKRWNPEV QYTSNYAKSA NVDFTVDNNG    720
LYTEPRPIGT RYLTRPL                                                  737
```

AAV CAPSIDS IDENTIFIED BY IN VIVO LIBRARY SELECTION

RELATED APPLICATIONS

This application is a continuation of U.S. application Ser. No. 17/050,475, filed Oct. 26, 2020, which is a national stage filing under 35 U.S.C. § 371 of international PCT application, PCT/US2019/029489, filed Apr. 26, 2019, which claims priority under 35 U.S.C. § 119(e) to U.S. provisional patent application, U.S. Ser. No. 62/663,988, filed Apr. 27, 2018, the entire contents of each of which are incorporated herein by reference.

REFERENCE TO AN ELECTRONIC SEQUENCE LISTING

The contents of the electronic sequence listing (U012070101US02-SEQ-KZM.xml; Size: 17,874 bytes; and Date of Creation: Aug. 24, 2022) is herein incorporated by reference in its entirety.

FIELD OF THE DISCLOSURE

The disclosure relates, in some aspects, to isolated nucleic acids, compositions, and kits comprising adeno-associated virus capsid proteins isolated following an in vivo capsid library selection. In some aspects, the disclosure relates to recombinant adeno-associated viruses (rAAVs) and methods of using the same.

BACKGROUND

Recombinant adeno-associated virus (AAV) vectors have emerged as a potent gene transfer platform for in vivo gene delivery. The first generation of AAV vectors to enter clinical trials were based on AAV2 capsid. Additional AAV capsids haven been identified from rhesus macaque and human tissues yielded a second generation of AAV vectors based on AAV 1. AAV9, and AAVrh10.

SUMMARY

The disclosure relates, in some aspects, to AAV capsids with tropism for human skeletal muscle. The disclosure is based, in part, on AAV capsid protein variants (e.g., variants of AAV clades E (AAV8) and A (AAV1/AAV6)) that are characterized by desirable functional properties, for example, highly efficient transduction of specific tissue/cell types, and/or low prevalence of neutralizing antibodies (NABs). In some embodiments, AAV capsids (and rAAVs comprising such capsids) are useful for treatment of certain diseases and disorders, such as muscular dystrophies (e.g., Duchenne muscular dystrophy (DMD), Becker muscular dystrophy, facioscapulohumeral muscular dystrophy, myotonic dystrophy, etc.).

Accordingly, in some aspects, the disclosure provides an isolated nucleic acid comprising the sequence set forth in SEQ ID NO: 1 or 2, or a fragment thereof. In some embodiments, an isolated nucleic acid encodes a polypeptide that is not identical to the sequence set forth in any one of SEQ ID NO: 3, 4, or 5 (e.g., wild-type AAV1, AAV6, or AAV8 capsid proteins, respectively).

In some aspects, the disclosure provides an isolated AAV capsid protein comprising the amino acid sequence set forth in SEQ ID NO: 6 or 7, or a fragment thereof. In some embodiments, the amino acid sequence of a peptide fragment is not identical to the sequence of any one of SEQ ID NOs: 3, 4, or 5 (e.g., wild-type AAV1. AAV6, or AAV8 capsid proteins, respectively). In some embodiments, the disclosure provides an isolated AAV capsid protein comprising a peptide fragment with an amino acid sequence that is not identical to the sequence of any one of SEQ ID NOs: 3, 4, or 5 (e.g., wild-type AAV1, AAV6, or AAV8 capsid proteins, respectively).

In some embodiments, an isolated AAV capsid protein is a VP1 capsid protein. In some embodiments, an isolated AAV capsid protein is a VP2 capsid protein. In some embodiments, an isolated AAV capsid protein is a VP3 capsid protein.

In some embodiments, an isolated nucleic acid sequence comprising the sequence set forth in SEQ ID NOs: 1 or 2 encodes a VP1 capsid protein. In some embodiments, an isolated nucleic acid sequence comprising the sequence set forth in SEQ ID NOs: 1 or 2 encodes a VP2 capsid protein. In some embodiments, an isolated nucleic acid sequence comprising the sequence set forth in SEQ ID NOs: 1 or 2 encodes a VP3 capsid protein.

In some aspects, the disclosure provides a recombinant expression vector (e.g. a plasmid, etc.) comprising a nucleic acid sequence encoding an isolated AAV capsid protein or a fragment thereof, as described by the disclosure (e.g., an isolated AAV capsid protein comprising the amino acid sequence set forth in SEQ ID NOs: 6 or 7, or a fragment thereof).

In some aspects, the disclosure provides a recombinant AAV (rAAV) comprising an AAV capsid protein (e.g., an isolated capsid protein) having the amino acid sequence set forth in SEQ ID NOs: 6 or 7, or a fragment thereof. In some embodiments, an rAAV comprises an isolated nucleic acid encoding a transgene flanked by one or more AAV inverted terminal repeats (ITRs).

In some aspects, the disclosure provides a composition comprising an isolated AAV capsid protein or a fragment thereof, as described herein. In some embodiments, a composition further comprises a pharmaceutically acceptable carrier.

In some aspects, the disclosure provides a composition comprising an rAAV as described herein (e.g., an rAAV comprising a capsid protein having the amino acid sequence set forth in SEQ ID NOs: 6 or 7, or a fragment thereof). In some embodiments, a composition further comprises a pharmaceutically acceptable carrier.

In some aspects, the disclosure provides a host cell containing a nucleic acid encoding a polypeptide comprising the sequence set forth in SEQ ID NOs: 1 or 2. In some embodiments, the disclosure provides a composition comprising a host cell as described herein and a sterile cell culture medium. In some embodiments, a composition comprising a host cell further comprises a cryopreservative.

In some aspects, the disclosure provides a host cell that contains an rAAV as described herein. In some embodiments, the composition further comprises a sterile cell culture medium. In some embodiments, the composition further comprises a cryopreservative.

In some aspects, the disclosure provides methods for delivering a transgene to a subject. In some embodiments, the methods comprise a step of administering an rAAV as described herein to a subject. In some embodiments of the methods, the rAAV comprises an isolated nucleic acid encoding at least one transgene. In some embodiments, the rAAV infects cells of a target tissue (e.g., muscle cells, muscle tissue, etc.) of a subject. In some embodiments, a target tissue is skeletal muscle. In some embodiments, a subject is a mouse, a rat, a rabbit, a dog, a cat, a sheep, a pig, or a non-human primate. In some embodiments, a subject is a human.

In some embodiments, at least one transgene encoded by the rAAV is a protein coding gene. In some embodiments, a protein coding gene encodes a therapeutic protein, for example a therapeutic protein useful for treating a muscular dystrophy (e.g., dystrophin, dystrophin, etc.). In some embodiments, a therapeutic protein is a secreted protein (e.g., alpha-antitrypsin (AAT), etc.). In some embodiments, a protein coding gene is a minigene (e.g., microdystrophin, micro-utophin, mini-dysferlin).

In some embodiments, at least one transgene encodes a small interfering nucleic acid (e.g., dsRNA, siRNA, shRNA, microRNA (miRNA), artificial miRNA (amiRNA), etc.). In some embodiments, a small interfering nucleic acid is a microRNA (miRNA). In some embodiments, a miRNA is expressed in a cell of a target tissue, for example a target tissue of a subject. In some embodiments, a small interfering nucleic acid is a miRNA sponge that inhibits the activity of a least one miRNA in the subject. In some embodiments, a target tissue is muscle tissue or muscle cells, for example skeletal muscle tissue or skeletal muscle cells.

In some embodiments, an rAAV is administered to a subject intravenously, transdermally, intraocularly, intrathecally, intracerebrally, orally, intramuscularly, subcutaneously, intranasally, or by inhalation.

In some embodiments, a transgene comprises an isolated nucleic acid encoding a protein that is operably linked to a tissue specific promoter. In some embodiments, a tissue-specific promoter is a skeletal muscle-specific promoter, such as human skeletal actin (HSA) or alpha skeletal actin (ACTA1) or muscle creatine kinase (MCK), or engineered muscle specific promoters such as the CK1-7 collection or the hybrid MHCK7 promoter.

In some aspects, the disclosure provides a kit for producing an rAAV as described herein (e.g., an rAAV comprising a capsid protein having the sequence set forth in SEQ ID NO: 6 or 7, or a fragment thereof). In some embodiments, a kit comprises a container housing an isolated nucleic acid comprising the sequence set forth in SEQ ID NO: 1 or 2. In some embodiments, a kit further comprises instructions for producing an rAAV. In some embodiments, a kit comprises at least one container housing an rAAV vector, wherein the vector comprises at least one transgene. In some embodiments, a container is a syringe.

In some aspects, the disclosure provides a pseudotyped rAAV, comprising a capsid protein, or a fragment thereof, as described by the disclosure, and an isolated nucleic acid comprising one or more AAV ITRs derived from a different AAV serotype than the capsid protein, wherein the one or more AAV ITRs flank a nucleic acid sequence encoding at least one transgene.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

DETAILED DESCRIPTION

Figure 1:
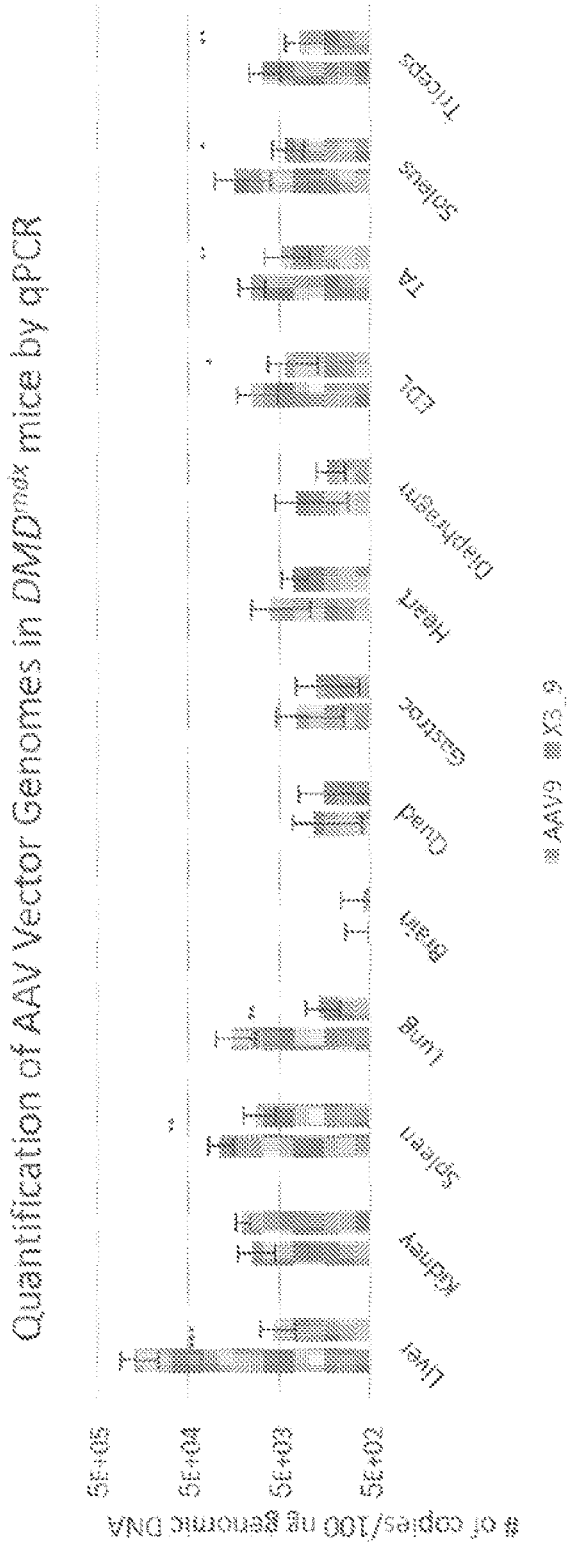
FIG. 1 shows qPCR gene expression quantification of muscle-identified AAV-X3_9 capsid genes in DMD$^{mdx}$ mice compared to AAV9 capsid gene expression.

Adeno-associated virus (AAV) is a small, replication-defective, non-enveloped virus that depends on the presence of a second virus, such as adenovirus, for its growth in cells. Generally. AAV does not cause disease and induces a very mild immune response in the host. AAV can infect both dividing and non-dividing cells and may incorporate its genome into that of the host cell. Taken together, these features make AAV an attractive candidate in generating viral vectors for gene therapy. Recombinant AAVs (rAAVs) based on capsid protein serotype 2 provided the proof-of-concept for non-toxic and stable gene transfer in murine and large animal models. However, these rAAVs have been observed, in some embodiments, to exhibit poor gene transfer in numerous major target tissues, including skeletal muscle.

The tropism of an AAV vector is primarily dictated by its capsid. As a result, methods for isolating novel AAVs have been largely focused on isolating DNA sequences for AAV capsids from target tissues. Previous work (U.S. Pat. No. 9,217,155, the contents of which are incorporated herein in their entirety) has demonstrated that endogenous AAVs are transcriptionally active in mammalian cells. The RNA produced by these AAVs can be subjected to reverse-transcription polymerase chain reaction (RT-PCR) to generate cDNA, which can be sequenced to identify the AAV capsid proteins expressed in a target tissue (e.g., muscle cells or muscle tissue, for example skeletal muscle cells or skeletal muscle tissue).

Accordingly, in some aspects, the disclosure relates to AAV capsid proteins isolated from a target tissue (e.g., skeletal muscle) following injection with a library of isolated nucleic acids used as templates for RT-PCR. In some embodiments, the isolated capsid proteins are useful for production of recombinant adeno-associated viruses (rAAVs) having increased tropism for the tissue from which they were originally isolated (e.g., skeletal muscle tissue).

Isolated AAV Capsid Proteins and Nucleic Acids

AAVs isolated from mammals, particularly non-human primates, are useful for creating gene transfer vectors for clinical development and human gene therapy applications. In some embodiments, recombinant AAVs (rAAVs) disclosed hemin have a tropism for skeletal muscle. Accordingly, in some embodiments, the rAAVs of the instant disclosure are particularly useful for gene therapy of skeletal muscle. In some embodiments, isolated AAV capsid proteins are provided that have been obtained using barcoded chimeric AAV capsid libraries.

The disclosure relates, in some aspects to AAV capsid protein variants that have been identified from muscle tissue (e.g., skeletal muscle tissue). In some embodiments, isolated capsid proteins described by the disclosure are AAV8 capsid protein variants or fragments thereof, or AAV1/AAV6 capsid protein variants or fragments thereof. As used herein. "variant" refers to a capsid protein that comprises one or more amino acid mutations (e.g., substitutions (non-sense, missense, conservative, non-conservative, etc.), insertions, deletions, etc.) relative to a naturally-occurring, wild-type capsid protein. In some embodiments, a variant has at least 1, at least 2, at least 3, at least 4, at least 5, at least 10, at least 20, at least 50, at least 100, at least 200, or at least 300 amino acid substitutions relative to a wild-type capsid protein. In some embodiments, the wild-type capsid protein sequences of AAV 1, AAV6, and AAV8 are represented by SEQ ID NOs: 3-5, respectively. In some embodiments, the amino acid sequence of an AAV capsid protein described herein is represented by SEQ ID NOs: 6 or 7. In some embodiments, an AAV capsid protein as described herein is encoded by a nucleic acid sequence set forth in SEQ ID NOs: 1 or 2.

In some embodiments, a fragment (portion) of an isolated nucleic acid encoding a AAV capsid sequence may be useful for constructing a nucleic acid encoding a desired capsid sequence. Fragments may be of any appropriate length (e.g., at least 6, at least 9, at least 18, at least 36, at least 72, at least 144, at least 288, at least 576, at least 1152 or more nucleotides in length). For example, a fragment of nucleic acid sequence encoding a polypeptide of a first AAV capsid protein may be used to construct, or may be incorporated within, a nucleic acid sequence encoding a second AAV capsid sequence to alter the properties of the AAV capsid. In some embodiments. AAV capsid proteins that comprise capsid sequence fragments from multiple AAV serotypes are referred to as chimeric AAV capsids.

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods. e.g., Molecular Cloning: A Laboratory Manual, J. Sambrook, et al., eds., Second Edition. Cold Spring Harbor Laboratory Press. Cold Spring Harbor. New York 1989, or Current Protocols in Molecular Biology, F. M. Ausubel, et al., eds., John Wiley & Sons. Inc., New York. Conservative substitutions of amino acids include substitutions made among amino acids within the following groups: (a) M, I, L, V; (b) F, Y, W: (c) K. R. H; (d) A, G; (e) S. T; (f Q, N; and (g) E. D. Therefore, one can make conservative amino acid substitutions to the amino acid sequence of the proteins and polypeptides disclosed herein.

As used herein, the term "nucleic acid" refers to polymers of linked nucleotides, such as DNA, RNA, etc. In some embodiments, proteins and nucleic acids of the disclosure are isolated. As used herein, the term "isolated" means artificially produced (e.g., an artificially produced nucleic acid, or an artificially produced protein, such ac a capsid protein). As used herein with respect to nucleic acids, the term "isolated" means: (i) amplified in vitro by, for example, polymerase chain reaction (PCR): (ii) recombinantly produced by cloning: (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been artificially produced (e.g., by chemical synthesis, by recombinant DNA technology, etc.).

"Homology" refers to the percent identity between two polynucleotides or two polypeptides. The term "substantial homology" when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences. When referring to a polypeptide, or fragment thereof, the term "substantial homology" indicates that, when optimally aligned with appropriate gaps, insertions or deletions with another polypeptide, there is nucleotide sequence identity in about 90 to 100% of the aligned sequences. The term "highly conserved" means at least 80% identity, preferably at least 90% identity, and more preferably, over 97% identity. In some cases, highly conserved may refer to 100% identity. Identity is readily determined by one of skill in the art by, for example, the use of algorithms and computer programs known by those of skill in the art.

As described herein, alignments between sequences of nucleic acids or polypeptides are performed using any of a variety of publicly or commercially available Multiple Sequence Alignment Programs, such as "Clustal W", accessible through Web Servers on the internet. Alternatively, Vector NTI utilities may also be used. There are also a number of algorithms known in the art which can be used to measure nucleotide sequence identity, including those contained in the programs described above. As another example, polynucleotide sequences can be compared using BLASTN, which provides alignments and percent sequence identity of the regions of the best overlap between the query and search sequences. Similar programs are available for the comparison of amino acid sequences. e.g., the "Clustal X" program. BLASTP. 1. Typically, any of these programs are used at default settings, although one of skill in the art can alter these settings as needed. Alternatively, one of skill in the art can utilize another algorithm or computer program which provides at least the level of identity or alignment as that provided by the referenced algorithms and programs. Alignments may be used to identify corresponding amino acids between two proteins or peptides. A "corresponding amino acid" is an amino acid of a protein or peptide sequence that has been aligned with an amino acid of another protein or peptide sequence. Corresponding amino acids may be identical or non-identical. A corresponding amino acid that is a non-identical amino acid may be referred to as a variant amino acid.

Alternatively, for nucleic acids, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

Recombinant AAVs

In some aspects, the disclosure provides isolated AAVs. As used herein with respect to AAVs, the term "isolated" refers to an AAV that has been artificially obtained or produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining the "tropism", or tissue-specific targeting capabilities of an AAV. Thus, an rAAV having a capsid appropriate for the tissue being targeted can be selected. In some embodiments, an rAAV comprises a capsid protein having an amino acid sequence as set forth in SEQ ID NOs: 6 or 7, or a protein having substantial homology thereto. In some embodiments, an rAAV comprises a capsid protein having an amino acid sequence that is 90% identical to SEQ ID NOs: 6 or 7, 80% identical to SEQ ID NOs: 6 or 7, 70% identical to SEQ ID NOs: 6 or 7, 60% identical to SEQ ID NOs: 6 or 7, or 50% identical to SEQ ID NOs: 6 or 7.

In some embodiments, the rAAVs of the disclosure are pseudotyped rAAVs. Pseudotyping is the process of producing viruses or viral vectors in combination with foreign viral envelope proteins. The result is a pseudotyped virus particle. With this method, the foreign viral envelope proteins can be used to alter host tropism or an increased/decreased stability of the virus particles. In some aspects, a pseudotyped rAAV comprises nucleic acids from two or more different AAVs, wherein the nucleic acid from one AAV encodes a capsid protein and the nucleic acid of at least one other AAV encodes other viral proteins and/or the viral genome. In some embodiments, a pseudotyped rAAV refers to an AAV comprising an inverted terminal repeats (ITRs) of one AAV serotype and an capsid protein of a different AAV serotype. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

Methods for obtaining recombinant AAVs having a desired capsid protein are well known in the art. (See, for example, US 2003/0138772, the contents of which are incorporated herein by reference in their entirety). Typically the methods involve culturing a host cell which contains a nucleic acid sequence encoding an AAV capsid protein (e.g., a nucleic acid having a sequence as set forth in any one of SEQ ID NOs: 1 and 2, or fragment thereof: a functional rep gene; a recombinant AAV vector composed of, AAV inverted terminal repeats (ITRs) and a transgene; and sufficient helper functions to permit packaging of the recombinant AAV vector into the AAV capsid proteins.

In some embodiments, the disclosure relates to a rAAV comprising a capsid protein identified by the methods disclosed herein. In some embodiments, the rAAV targets muscle tissue of a subject. Examples of muscle tissue include but are not limited to skeletal muscle, smooth muscle, and cardiac muscle. In some embodiments, the rAAV targets muscle cells. Examples of muscle cells include but are not limited to myocytes (e.g., cardiac myocytes, skeletal myocytes, etc.), myocardial cells, myofibril cells, sarcomere cells, etc.

In some embodiments, an rAAV further comprises a transgene. In some embodiments, the transgene encodes a therapeutic protein (e.g., a protein useful for treating a particular disease). Examples of therapeutic proteins include dystrophin (useful for treating Duchenne muscular dystrophy), dysferlin (useful for treating limb-girdle muscular dystrophy type 2B), SOD1 (useful for treating amyotrophic lateral sclerosis), etc. In some embodiments, the transgene is a skeletal muscle-associated gene. Examples of skeletal muscle-associated genes include but are not limited to dysferlin, dystrophin, etc. In some embodiments, a therapeutic protein is a secreted protein, for example SOD1, erythropoietin (EPO), insulin, interferon, etc. In some embodiments, a transgene is an interfering RNA, for example a skeletal muscle-associated shRNA, miRNA, or amiRNA.

Methods for obtaining recombinant AAVs having a desired capsid protein are well known in the art. (See, for example, US 2003/0138772, the contents of which are incorporated herein by reference in their entirety). Typically the methods involve culturing a host cell which contains a nucleic acid sequence encoding an AAV capsid protein (e.g., a nucleic acid encoding a polypeptide having a sequence as set forth in any one of SEQ ID NOs: 1 or 2) or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by a cap gene of an AAV. In some embodiments, AAVs comprise three capsid proteins, virion proteins 1 to 3 (named VP1, VP2 and VP3), all of which may be expressed from a single cap gene. Accordingly, in some embodiments, the VP1. VP2 and VP3 proteins share a common core sequence. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the protein shell is primarily comprised of a VP3 capsid protein. In some embodiments, the functions of the capsid proteins are to protect the viral genome, deliver the genome and interact with the host. In some aspects, capsid proteins deliver the viral genome to a host in a tissue specific manner. In some embodiments, VP1 and/or VP2 capsid proteins may contribute to the tissue tropism of the packaged AAV. In some embodiments, the tissue tropism of the packaged AAV is determined by the VP3 capsid protein. In some embodiments, the tissue tropism of an AAV is enhanced or changed by mutations occurring in the capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided hemin, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See. e.g., Sambrook et al, Molecular Cloning: A Laboratory Manual. Cold Spring Harbor Press. Cold Spring Harbor. New York. Similarly, methods of generating rAAV virions are well known and the selection of a suitable method is not a limitation on the disclosure. See, e.g., K. Fisher et al, J. Viol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See. e.g., Graham et al, (1973) Virology. 52:456. Sambrook et al. (1989) Molecular Cloning, a laboratory manual. Cold Spring Harbor Laboratories, New York, Davis et al. (1986) Basic Methods in Molecular Biology, Elsevier. and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVS. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product (e.g., a therapeutic protein or therapeutic minigene) or inhibitory RNA (e.g., shRNA, miRNA, amiRNA, miRNA inhibitor) from a transcribed gene.

The foregoing methods for packaging recombinant vectors in desired AAV capsids to produce the rAAVs of the disclosure are not meant to be limiting and other suitable methods will be apparent to the skilled artisan.

Recombinant AAV vectors

"Recombinant AAV (rAAV) vectors" of the disclosure are typically composed of, at a minimum, a transgene and its regulatory sequences, and 5 and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (Sec. e.g., B. J. Carter, in "Handbook of Parvoviruses", ed., P. Tijsser, CRC Press. pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual". 2d ed., Cold Spring Harbor Laboratory, New York (1989); and K. Fisher et al., J Virol., 70:520 532 (1996)). An example of such a molecule employed in the disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g., AAV2/1 has the IRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein. "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation. (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or mow proteins having been translated in frame. In some embodiments, operably linked coding sequences yield a fusion protein. In some embodiments, operably linked coding sequences yield a functional RNA (e.g., mRNA, shRNA, miRNA, miRNA inhibitor, etc.).

For nucleic acids encoding proteins, a polyadenylation sequence generally is inserted following the transgene sequences and before the Y AAV ITR sequence. A rAAV construct useful in the disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (1RES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al. and references cited therein at, for example, pages 3.18 3.26 and 16.17 16.27 and Ausubel et al., Current Protocols in Molecular Biology, John Wiley & Sons. New York. 1989]. In some 13 embodiments, a Foot and Mouth Disease Virus 2A sequence is included in polyprotein; this is a small peptide (approximately 18 amino acids in length) that has been shown to mediate the cleavage of polyproteins (Ryan. M D et al., EMBO, 1994; 4: 928-933; Mattion. N M et al., J Virology, November 1996; p. 8124-8127; Furler, S et al., Gene Therapy. 2001: 8: 864-873; and Halpin, C et al., The Plant Journal. 1999; 4: 453459). The cleavage activity of the 2A sequence has previously been demonstrated in artificial systems including plasmids and gene therapy vectors (AAV and retroviruses) (Ryan. M D et al., EMBO, 1994; 4: 928-933; Mattion. N M et al., J Virology. November 1996: p. 8124-8127; Furler, S et al., Gene Therapy. 2001; 8: 864-873; and Halpin, C et al., The Plant Journal, 1999; 4: 453-459: de Felipe, P et al., Gene Therapy, 1999; 6: 198-208: de Felipe. P et al., Human Gene Therapy, 2000:11: 1921-1931.; and Klump. H et al., Gene Therapy. 2001; 8: 811-817).

The precise nature of the regulatory sequences needed for gene expression in host cells may vary between species, tissues or cell types, but shall in general include, as necessary. 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al. Cell. 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, invitrogen. Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (Noel al, Proc. Natl. Acad. Sci. USA. 93:3346-3351 (1996)), the tetracycline-repressible system (Gossen et al, Proc. Natl. Acad. Sci. USA, 89:5547-5551 (1992)), the tetracycline-inducible system (Gossen et al. Science. 268:1766-1769 (1995), see also Harvey et al. Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In some embodiments, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: the skeletal muscle promoters human skeletal actin (HSA) and actin α-1 skeletal muscle (ACTA1), a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter. Sandig et al., Gene Ther., 3:1002-9 (1996); alpha-fetoprotein (AFP) promoter. 13 Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)). CD2 promoter. (Hansal et al., J. Immunol., 161:1063-8 (1998); immunoglobulin heavy chain promoter, T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA. 88:5611-5 (1991)), and the neuron-specific vgf gene promoter (Piccioli et al., Neuron. 15:373-84 (1995)), among others which will be apparent to the skilled arthsan.

In some embodiments, a tissue-specific promoter is a muscle-specific promoter. Examples of muscle-specific promoters include but are not limited to skeletal muscle promoters human skeletal actin (HSA), actin α-1 skeletal muscle (ACTA 1), muscle creatine kinase (MCK) promoter, unc45b promoter, troponin I promoter. Pitx3 promoter CK1-CK7 variants of creatine kinase promoter as well as hybrid promoters such as MHCK7, etc.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Reporter sequences that may be provided in a transgene include, without limitation. DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for 1-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of an rAAV.

In some aspects, the disclosure provides rAAV vectors for use in methods of preventing or treating one or more genetic deficiencies or dysfunctions in a mammal, such as for example, a polypeptide deficiency or polypeptide excess in a mammal, and particularly for treating or reducing the severity or extent of deficiency in a human manifesting one Or more of the disorders linked to a deficiency in such polypeptides in cells and tissues. The method involves administration of an rAAV vector that encodes one or more therapeutic peptides, polypeptides, siRNAs, microRNAs, antisense nucleotides, etc. in a pharmaceutically-acceptable carrier to the subject in an amount and for a period of time sufficient to treat the deficiency or disorder in the subject suffering from such a disorder.

Thus, the disclosure embraces the delivery of rAAV vectors encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include AAT1, BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1. IL-2, IL-3, IL-4, IL-5, IL-6, IL-7, IL-8, IL-9, IL-10, IL-10(187A), viral IL-10, IL-11 IL-12, IL-13, IL-14, IL-15, IL-16 IL-17, and IL-18.

The rAAV vectors may comprise a gene to be transferred to a subject to treat a disease associated with reduced expression, lack of expression or dysfunction of the gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia: phenylalanine hydroxylase, associated with phenylketonuria; branched chain alpha-ketoacid dehydrogenase, associated with Maple syrup urine disease; fumarylacetoacetate 13 hydrolase, associated with tyrosinemia type 1; methylmalonyl-CoA mutase, associated with methylmalonic acidemia; medium chain acyl CoA dehydrogenase, associated with medium chain acetyl CoA deficiency; omithine transcarbamylase, associated with omithine transcarbamylase deficiency; argininosuccinic acid synthetase, associated with citrullinemia: low density lipoprotein receptor protein, associated with familial hypercholesterolemia: UDP-glucuronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-galactosidase, associated with GM 1 gangliosidosis: beta-hexosaminidase A and B, associated with Tay-Sachs disease and Sandhoff disease; beta-glucocerebrosidase, associated with Gaucher disease; beta-glucuronidase, associated with Sly syndrome: peroxisome membrane protein 70 kDa, associated with Zellweger syndrome; porphobilinogen deaminase, associated with acute intermittent *porphyria*; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (A ADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure: a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; SERPINA for the treatment of alpha-1 antitrypsin deficiency; and, insulin for the treatment of diabetes.

In some embodiments, the rAAV vectors may comprise a gene encoding an antigen-binding protein, such as an immunoglobulin heavy chain or light chain or fragment thereof. e.g., that may be used for therapeutic purposes. In some embodiments, the protein is a single chain Fv fragment or Fv-Fc fragment. Accordingly, in some embodiments, the rAAV can be used to infect cells are of target tissue (e.g., muscle tissue) to engineer cells of the tissue to express an antigen-binding protein, such as an antibody or fragment thereof. In some embodiments, to 13 generate rAAVs that express the antibodies or antigen binding fragments, cDNAs engineered to express such proteins will be subcloned into an appropriate plasmid backbone and packaged into an rAAV.

In some embodiments, the rAAV comprises a transgene that encodes a minigene. As used herein. "minigene" refers to an isolated nucleic acid sequence encoding a recombinant peptide or protein where one or more non-essential elements of the corresponding gene encoding the naturally-occurring peptide or protein have been removed and where the peptide or protein encoded by the minigene retains function of the corresponding naturally-occurring peptide or protein. A "therapeutic minigene" refers to a minigene encoding a peptide or protein useful for treatment of a genetic disease, for example dystrophin, dysferlin. Factor VIII, Amyloid precursor protein (APP), Tyrosinase (Tyr), etc. Minigenes are known in the art and are described, for example by Karpati and Acsadi (1994) Clin Invest Med 17(5):499-509; Plantier et al. (2001) *Thromb Haemost*. 86(2):596-603; and Xiao et al. (2007) World J. *Gasrtroenterol*. 13(2):244-9.

Generally, an isolated nucleic acid encoding a minigene (e.g., a therapeutic minigene) is between about 10% and about 99% (e.g., about 10%, about 15%, about 20%, about 25%, about 30%, about 40% about 50%, about 60%, about 70%, about 75%, about 80%, about 90%, about 99%, etc. truncated with respect to a nucleic acid sequence encoding the corresponding naturally-occurring wild-type protein. For example, in some embodiments, a minigene encoding a CEP290 protein fragment is about 76% truncated (e.g., comprises about 24% of the nucleic acid sequence) compared to a wild-type CEP290 gene.

In some embodiments, the rAAV vectors may comprise a gene or genes encoding genome editing enzymes or related molecules. As used herein, "genome editing," refers to adding, disrupting or changing genomic sequences (e.g., a gene sequence). In some embodiments, genome editing is performed using engineered proteins and related molecules. In some aspects, genome editing comprises the use of engineered nucleases to cleave a target genomic locus. In some embodiments, genome editing further comprises inserting, deleting, mutating or substituting nucleic acid residues at a cleaved locus. In some embodiments, inserting, deleting, mutating or substituting nucleic acid residues at a cleaved locus is accomplished through endogenous cellular mechanisms such as homologous recombination (HR) and non-homologous end joining (NHEJ). Exemplary genome editing technologies include, but are not limited to Transcription Activator-like Effector Nucleases (TALENs), Zinc Finger Nucleases (ZFNs), engineered meganuclease re-engineered homing endonucleases and the CRISPR/Cas system. In some embodiments, the rAAV may comprise a gene or genes encoding proteins or molecules related to TALENs, including but not limited to transcription activator-like effectors (TALEs) and restriction endonucleases (e.g., FokI). In some embodiments, the rAAV may comprise a gene or genes encoding proteins or molecules related to ZFNs, including but not limited to proteins comprising the Cys2His2 fold group (for example Zif268 (EGR1)), and restriction endonucleases (e.g., FokI). In some embodiments, the rAAV may comprise a gene or genes encoding proteins or molecules related to the CRISPR/Cas system, including but not limited to Cas9, Cas6, dCas9, CRISPR RNA (crRNA) and trans-activating crRNA (tracrRNA).

The rAAVs of the disclosure can be used to restore the expression of genes that are reduced in expression, silenced, or otherwise dysfunctional in a subject (e.g., a tumor suppressor that has been silenced in a subject having cancer). The rAAVs of the disclosure can also be used to knockdown the expression of genes that are aberrantly expressed in a subject (e.g., an oncogene that is expressed in a subject having cancer). In some embodiments, an rAAV vector comprising a nucleic acid encoding a gene product associated with cancer (e.g., tumor suppressors) may be used to treat the cancer, by administering a rAAV harboring the rAAV vector to a subject having the cancer. In some embodiments, an rAAV vector comprising a nucleic acid encoding a small interfering nucleic acid (e.g., shRNAs, miRNAs) that inhibits the expression of a gene product associated with cancer (e.g., oncogens) may be used to treat the cancer, by administering a rAAV harboring the rAAV vector to a subject having the cancer. In some embodiments, an rAAV vector comprising a nucleic acid encoding a gene product associated with cancer (or a functional RNA that inhibits the expression of a gene associated with cancer) may be used for research purposes, e.g., to study the cancer or to identify therapeutics that treat the cancer. The following is a non-limiting list of exemplary genes known to be associated with the development of cancer (e.g., oncogenes and tumor suppressors): AARS, ABCB1, ABCC4, AB12, ABL1, ABL2, ACK1, ACP2, ACY1, ADSL, AK1, AKRIC2, AKT1, ALB, ANPEP, ANXA5, ANXA7, AP2MI, APC, ARHGAP5, ARHGEF5, ARID4A, ASNS, ATF4, ATM, ATP5B, ATP5O, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5. CCYR61. CD24. CD44. CD59, CDC20, CDC25, CDC25A, CDC25B, CDC2L5, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAF1A, CIB1. CKMT1, CLK1, CLK2, CLK3, CLNS1A, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR 1, EIF5, EPHA2, ERBB2, ERBB3, ERBB4, ERCC3, ETV1, ETV3. ETV6, F2R, FASTK, FBN1, FBN2, FES, FGFR1, FGR, FKBP8, FN1, FOS, FOSL1, FOSL2, FOXG1A, FOXO1A, FRAP1, FRZB, FTL, FZD2, FZD5, FZD9, G22P1. GAS6, CCN5L2, GDF15, GNA13, GNAS, GNB2, GNB2L1, GPR39, GRB2, GSK3A, GSPT1, GTF21, HDAC1. HDGF, HMMR, HPRT1, HRB, HSPA4, HSPA5, HSPA8, HSPB1, HSPH1, HYAL1, HYOU1. ICAM1, ID1, ID2, IDUA, IER3, IFITM1, IGF1R, IGF2R, IGFBP3, IGFBP4, IGFBP5, IL1B, ILK, ING1, IRF3, ITGA3, ITGA6, ITGB4, JAK1, JARID1A, JUN, JUNB, JUND, K-ALPHA-1, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINJ1, NMBR, NME1, NME2, NME3, NOTCH1, NOTCH2, NOTCH4, NPM1, NQO1, NR1D1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PP1H, PPP1CA, PPP2R5A, PRDX2, PRDX4, PRKAR1A, PRKCBP1, PRNP, PRSS15, PSMA1, PTCH, PTEN, PTGS1, PTMA, PTN, PTPRN, RAB5A, RAC, RAD50, RAF1, RALBP1, RAP1A, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6 KB1, RRM1, SARS, SELENBP1, SEMA3C, SEMA4D, SEPP1, SERPINH1, SFN, SFPQ, SFRS7, SHB, SHH, SIAH2, SIVA, SIVA TP53, SKI, SKIL, SLCI6A1, SLCIA4, SLC20A1, SMO, SMPD1, SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFBI, TGFBR2, TGFBR3, THBSI1, TIE, TIMP1, TIMP3, TJP1, TK1, TLE1, TNF, TNFRSF10A, TNFRSF10B, TNFRSF1A, TNFRSF1B, TNFRSF6, TNFSF7, TNK1, TOB1, TP53, TP53BP2, TP53I3, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCC1, YES1, YWHAB, YWHAZ, ZAP70, and ZNF9.

A rAAV vector may comprise as a transgene, a nucleic acid encoding a protein or functional RNA that modulates apoptosis. The following is a non-limiting list of genes associated with apoptosis and nucleic acids encoding the products of these genes and their homologues and encoding small interfering nucleic acids (e.g., shRNAs, miRNAs) that inhibit the expression of these genes and their homologues are useful as transgenes in certain embodiments of the disclosure: RPS27A. ABL1, AKT1, APAF1, BAD, BAG1, BAG3, BAG4, BAK1, BAX, BCL10, BCL2, BCL2A1, BCL2LI, BCL2L10, BCL2L11, BCL2L12, BCL2L13, BCL2L2, BCLAF1, BFAR, BID, BIK, NAIP, BIRC2, BIRC3, XIAP, BIRC5, BIRC6, BIRC7, BIRC8, BNIP1, BNIP2, BNIP3, BNIP3L, BOK, BRAF, CARD10, CARD 11, NLRC4, CARD14, NOD2, NOD1, CARD6, CARD8, CARD9, CASP1, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGF1R, LTA, LTBR, MCL1, NOL3, PYCARD, RIPK1, RIPK2, TNF, TNFRSF10A, TNFRSF10B, TNFRSF10C, TNFRSF10D, TNFRSF11B, TNFRSF12A, TNFRSF14, TNFRSF19, TNFRSF1A, TNFRSF1B, TNFRSF2L, TNFRSF25, CD40, FAS, TNFRSF6B, CD27, TNFRSF9, TNFSF10, TNFSF14, TNFSF18, CD40LG, FASLG, CD70, TNFSF8, TNFSF9, TP53, TP53BP2, TP73, TP63, TRADD, TRAF1, TRAF2, TRAF3, TRAF4, and TRAF5.

In some aspects, the disclosure relates to methods and compositions for treating skeletal muscle-related disorders. As used herein, a "skeletal muscle-related disorder" is a disease or condition of the skeletal muscle. A skeletal muscle-related disorder may be of a genetic origin, either inherited or acquired through a somatic mutation. A skeletal muscle-related disorder may be an inflammatory myopathy characterized by inflammation and progressive weakening of muscles. A skeletal muscle-related disorder may also be a cancer of the skeletal muscle. A skeletal muscle-related disorder that is a cancer may be a primary cancer of the skeletal muscle, e.g., a rhabdomyosarcoma, etc., or may be a cancer that has metastasized to skeletal muscle tissue. e.g., a lung cancer that has metastasized to the skeletal muscle. Further non-limiting examples of skeletal muscle-related disorders include: spinal muscular atrophy, muscular dystrophies (e.g., Duchenne muscular dystrophy, Becker muscular dystrophy, Miyoshi myopathy, facioscapulohumeral muscular dystrophy, myotonic dystrophy, etc.), McArdle disease, and inclusion body myositis.

In some embodiments, the disclosure relates to a rAAV vector comprising a transgene, a nucleic acid encoding a protein or functional RNA useful for the treatment of a condition, disease or disorder associated with skeletal muscle tissue. Examples of genes associated with skeletal muscle disease include but are not limited to TTN, DMD associated with muscular dystrophy; and SMN1, UBE1, DYNC1H1 associated with spinal muscular atrophy, ACTA1 associated with congenital myopathy, and PYGM associated with McArdle disease.

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

Useful transgene products also include miRNAs, miRNAs and other small interfering nucleic acids regulate gene expression via target RNA transcript cleavage/degradation or translational repression of the target messenger RNA (mRNA), miRNAs are natively expressed, typically as final 19-25 non-translated RNA products, miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as transgenes or as targets for small interfering nucleic acids encoded by transgenes 0 e.g., miRNA sponges, antisense oligonucleotides. TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7c, hsa-let-7c*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-1066, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR -1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135h*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, ha-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-4*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-Sp, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-Sp, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, h-a-miR-210, hsa-miR-21.1, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, h a-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, h-a-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, 1sa-miR-30c, hsa-miR-30c-1*, hsa-miR-30c-2*,hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, h-a-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR,-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378- hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-50), hsa-miR-500*, hsa-miR-501-3p, hsa-miR-501-5p, hsa-miR-502-3p, hsa-miR-502-5p- hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c, hsa-miR-51&1-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-Sp, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548h-5p, hsa-miR-548c-3p, hsa-miR-548c-5p, hsa-miR-548d-3p, hsa-miR-548d-135p, hsa-miR-548c, hsa-miR-548f, hsa-miR-548g, hsa-miR-5481i, 1hsa-miR-548i, hsa-miR-548j, hsa-miR-548k, hsa-miR-5481, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, 2t hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR- 576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, -3, -hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR,-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*1, hsa-miR-885-3p, hsa-miR-885-5p, hsa-miR-886-3p, hsa-miR-886-5p, hsa-miR-887, hsa-miR-888, hsa-MiR-888*, 1hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92α-1*, hsa-miR-92a-2*, hsa-miR-92h, hsa-13 miR-92b*, hsa-miR-93, hsa-miR-93*, hsa-miR-933, hsa-miR-934, hsamiR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*.

A miRNA inhibits the function of the mRNAs it targets and, as a result, inhibits 2t expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge. TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

A "miRNA Inhibitor" is an agent that blocks miRNA function, expression and/or processing. For instance, these molecules include but are not limited to microRNA specific antisense, microRNA sponges, tough decoy RNAS (TuD RNAs) and microRNA oligonucleotides (double-stranded, hairpin, short oligonucleotides) that inhibit miRNA interaction with a Drosha complex. MicroRNA inhibitors can be expressed in cells from a transgenes of a rAAV vector, as discussed above. MicroRNA sponges specifically inhibit miRNAs through a complementary heptameric seed sequence (Ebert. M.S. Nature Methods, Epub August, 12, 2007). In some embodiments, an entire family of miRNAs can be silenced using a single sponge sequence. TuD RNAs achieve efficient and long-term-suppression of specific miR-NAs in mammalian cells (See, e.g., Takeshi Haraguchi, et al., Nucleic Acids Research, 2009, Vol. 37. No. 6 e43, the contents of which relating to TuD RNAs are 1.5 incorporated herein by reference). Other methods for silencing miRNA function (derepression of miRNA targets) in cells will be apparent to one of ordinary skill in the art.

In some embodiments, the cloning capacity of the recombinant RNA vector may limited and a desired coding sequence may require the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Recombinant AAV Administration Methods

The rAAVs may be delivered to a subject in compositions according to any appropriate methods known in the art. The rAAV, preferably suspended in a physiologically compatible carrier (e.g., in a composition), may be administered to a subject, e.g., host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177, 403, can also be employed by the skilled artisan to administer the virions into the vasculature of an isolated limb to potentially enhance transduction into muscle cells or tissue.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect." e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary between animals or tissues. For example, an effective amount of the rAAV is generally in the range of from about 1 ml to about 100 ml of solution containing from about $10^9$ to $10^{16}$ genome copies. In some embodiment(the rAAV is administered at a dose of $10^{10}$, $10^{11}$, $10_{12}$, $10^{13}$, $10^{14}$, or $10^{15}$ genome copies per subject. In some embodiments the rAAV is administered at a dose of $10^{10}$, $10^{11}$, $10^{12}$, $10^{13}$, or $10^{14}$ genome copies per kg. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., ~$10^{13}$GC/ml or more). Methods for reducing aggregation of rAAVs are well-known in the art and, include, for example, addition of surfactants, pH adjustment, salt concentration adjustment, etc. (See, e.g., Wright FR. et al., Molecular Therapy (2005) 12, 171-178, the content- of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158: 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213, 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 p m. Sonication of MLVs results in the formation of small unilamellar vesicles (SUVs) with diameters in the range of 200 to 500.ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or mom containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder.) In certain cases, some of the compositions may be constitutable or otherwise processable (e.g., to an active form), for example, by the addition of a suitable solvent or other species (for example, water or a cell culture medium), which may or may not be provided with the kit. As used herein. "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.). Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or mom of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1: Generation of an AAV Capsid Library Isolated from Human Muscle

This Example describes AAV capsid genes that were subjected to molecular evolution to generate new entities with enhanced properties to target particular cell types or tissues. A DNA-shuffled AAV capsid library with ~2×10 unique members was injected into the tail vein of NOD-Rag1$^{null}$IL2r$\gamma^{null}$ immunodeficient mice with an engrafted human donor muscle in one hindlimb. Three doses were injected and mice were sacrificed 4 weeks post-injection. Genomic DNA was isolated from the human xenograft in each dose group, and AAV capsids were PCR amplified from these samples and sequenced.

After one selection round, 2 capsid sequences were initially identified, representing a range of parental capsid combinations. The capsids. AAV-X3_9 (SEQ ID NO: 6) and AAV-X4_10 (SEQ ID NO: 7), are most closely related to the parental AAV8 and AAV1/AAV6 capsids, respectively.

Recombinant AAV vectors encoding GFP were produced and tested first in cell culture. The vectors encoding AAV-X3_9. AAV-X4_10, and AAV9 capsid genes and GFP were injected into C57BL/6J and DMD$^{null}$ mice at 5×10$^{13}$ vg/kg for biodistribution and GFP 13 expression. Strikingly, the AAV-X3_9 capsids demonstrate lower transduction of spleen, liver, and lung than AAV9 capsids (FIG. 1).

Figure 2:
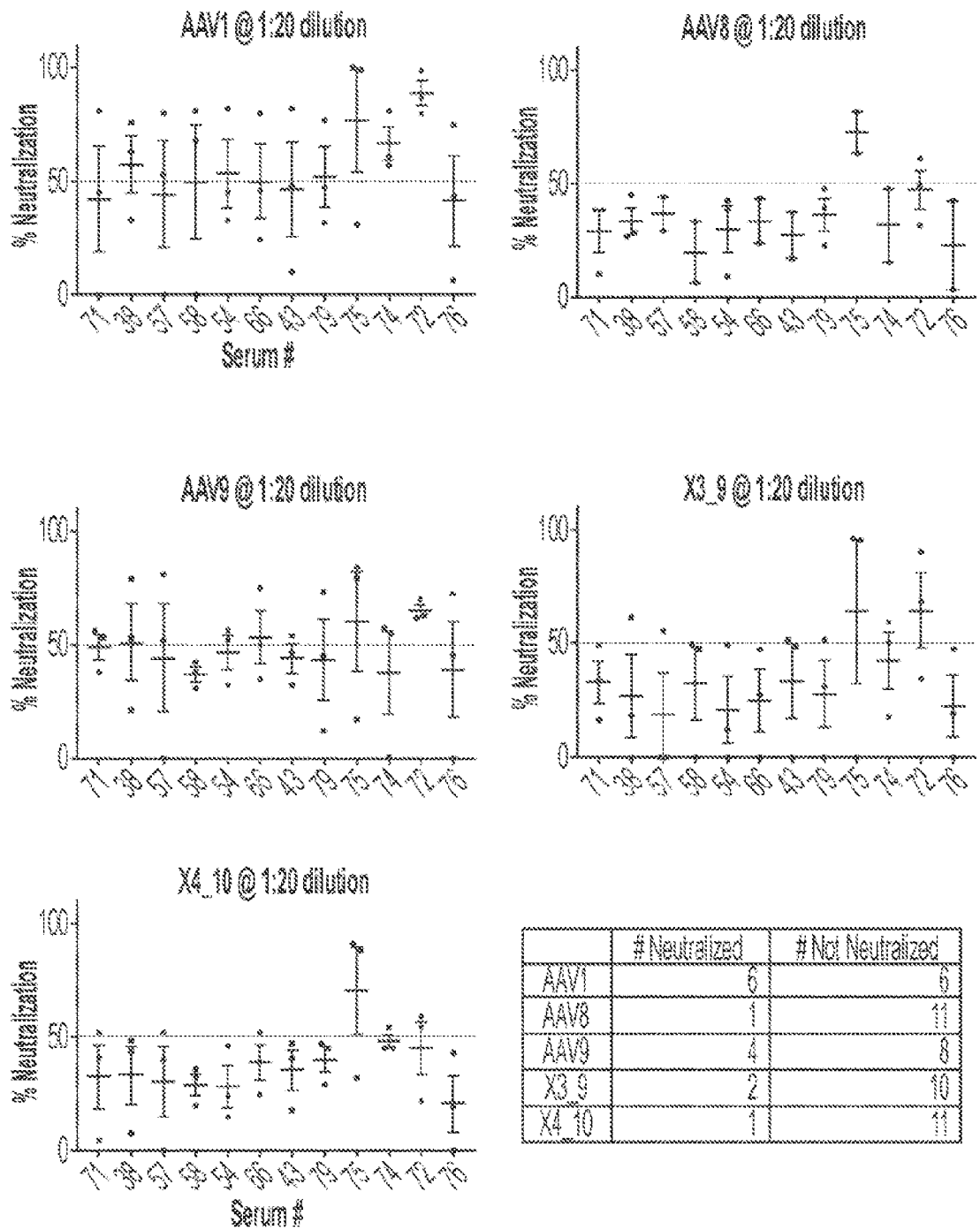
FIG. 2 shows comparative data for neutralization of AAV-X3_9 and AAV-X4_10 capsid proteins and AAV1, AAV8, and AAV9 capsid proteins by a random set of 12 healthy donor sera.

The human serum neutralization profiles of AAV-X3_9 and AAV-X4_10 were compared to AAV1, AAV8 (closest related parental capsids, respectively) and AAV9. Both AAV-X3_9 and AAV-X4_10 show less neutralization with human serum from 12 healthy donors that AAV1 or AAV9 (FIG. 2).

EQUIVALENTS

While several embodiments of the present invention have been described and illustrated herein, those of ordinary skill in the an will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined. i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B): in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list. "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims. "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or mom elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B." or, equivalently "at least one of A and/or B") can refer, in one embodiment, to at least one, optionally including more than one. A, with no B present (and optionally including elements other than B); in another embodiment, to at least one, optionally including more than one, B, with no A present (and optionally including elements other than A); in yet another embodiment, to at least one, optionally including more than one. A. and at least one, optionally including more than one. B (and optionally including other elements), etc.

In the claims, as well as in the specification above, all transitional phrases such as "comprising," "including." "carrying." "having." "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first" "second," "third." etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements,

```
SEQUENCES
SEQ ID NO 1: nucleic acid sequence encoding the AAV-X3_9
capsid protein
ATGGCTGCCGATGGTTATCTTCCAGATTGGCTCGAGGACAACCTCTCTGAGGGCATT

CGCGAGTGGTGGGCGCTGAAACCTGGAGCCCCGAAGCCCAAAGCCAACCAGCAAA

AGCAGGACGACGGCCGGGGTCTGGTGCTTCCTGGCTACAAGTACCTCGGACCCTTC

AACGGACTCGACAAGGGGGAGCCCGTCAACGCGGCGGACGCAGCGGCCCTCGAGC

ACGACAAGGCCTACGACCAGCAGCTGCAGGCGGGTGACAATCCGTACCTGCGGTAT

AACCACGCCGACGCCGAGTTTCAGGAGCGTCTGCAAGAAGATACGTCTTTTGGGGG

CAACCTCGGGCGAGCAGTCTTCCAGGCCAAGAAGCGGGTTCTCGAACCTCTCGGTC

TGGTTGAGGAAGGCGCTAAGACGGCTCCTGGAAAGAAGAGACCAGTAGAGCAGTC

ACCCCAAGAACCAGACTCCTCCTCGGGCATCGGCAAGAAAGGCCAACAGCCCGCCA

GAAAAAGACTCAATTTTGGTCAGACTGGCGACTCAGAGTCAGTCCCCGATCCACAA

CCTCTCGGAGAACCTCCAGCAGCCCCCTCAGGTCTGGGACCTAATACAATGGCTTCA

GGCGGTGGCGCTCCAATGGCAGACAATAACGAAGGCGCCGACGGAGTGGGTAATT

CCTCGGGAAATTGGCATTGCGATTCCACATGGCTGGGCGACAGAGTCATCACCACC

AGCACCCGAACCTGGGCCCTGCCCACCTACAACAACCACCTCTACAAGCAAATATC

CAATGGGACATCGGGAGGAAGCACCAACGACAACACCTACTTCGGCTACAGCACCC

CCTGGGGGTATTTTGACTTCAACAGATTCCACTGCCACTTTTCACCACGTGACTGGC

AGCGACTCATCAACAACAACTGGGGATTCCGGCCCAAGAGACTCAGCTTCAAGCTC

TTCAACATCCAGGTCAAGGAGGTCACGCAGAATGATGGCGTCACAACCATCGCTAA

TAACCTTACCAGCACGGTTCAAGTCTTCTCGGACTCGGAGTACCAGCTTCCGTACGT

CCTCGGCTCTGCGCACCAGGGCTGCCTCCCTCCGTTCCCGGCGGACGTGTTCATGAT

TCCGCAATACGGCTACCTGACGCTCAACAATGGCAGCCAAGCCGTGGGACGTTCAT

CCTTTTACTGCCTGGAATATTTCCCATCGCAGATGCTGAGAACGGGCAATAACTTTA

CCTTCAGCTACACCTTCGAGGACGTGCCTTTCCACAGCAGCTACGCGCACAGCCAG

AGCCTGGACCGGCTGATGAATCCTCTCATCGACCAGTACCTGTATTACCTGAACAGA

ACTCAGAATCAGTCCGGAAGTGCCCAAAACAAGGACTTGCTGTTTAGCCGGGGGTC

TCCAGCTGGCATGTCTGTTCAGCCCAAAAACTGGCTACCTGGACCCTGTTATCGGCA

GCAGCGCGTTTCTAAAACAAAAACAGACAACAACAACAGCAATTTTACCTGGACTG

GTGCTTCAAAATATAACCTCAATGGGCGTGAATCCATCATCAACCCTGGCACTGCTA

TGGCCTCACACAAAGACGACGAAGACAAGTTCTTTCCCATGAGTGGTGTCATGATTT

TTGGAAAAGAGAGCGCCGGAGCTTCAAACACTGCATTGGACAATGTCATGATTACA

GACGAAGAGGAAATTAAAGCCACTAACCCTGTGGCCACCGAAAGATTTGGGACCGT

GGCAGTCAATTTCCAGAGCAGCAGCACAGACCCTGCGACCGGAGATGTGCATGTTA

TGGGAGCCTTACCTGGAATGGTGTGGCAAGACAGAGACGTATACCTGCAGGGTCCT

ATTTGGGCCAAAATTCCTCACACGGATGGACACTTTCACCCGTCTCCTCTCATGGGC

GGCTTTGGACTTAAGCACCCGCCTCCTCAGATCCTCATCAAAAACACGCCTGTTCCT
```

-continued

GCGAATCCTCCGGCAGAGTTTTCGGCTACAAAGTTTGCTTCATTCATCACCCAGTAT

TCCACAGGACAAGTGAGCGTGGAGATTGAATGGGAGCTGCAGAAAGAAAACAGCA

AACGCTGGAATCCCGAAGTGCAGTATACATCTAACTATGCAAAATCTGCCAACGTT

GATTTCACTGTGGACAACAATGGACTTTATACTGAGCCTCGCCCCATTGGCACCCGT

TACCTCACCCGTCCCCTGTAA

SEQ ID NO 2: nucleic acid sequence encoding the AAV-X4_10 capsid protein
ATGGCTGCCGATGGTTATCTTCCAGATTGGCTCGAGGACAACCTCTCTGAGGGCATT

CGCGAGTGGTGGGACCTGAAACCTGGAGCCCCCAAGCCCAAGGCCAACCAGCAGA

AGCAGGACGACGGCCGGGGTCTGGTGCTTCCTGGCTACAAGTACCTCGGACCCTTC

AACGGACTCGACAAGGGGGAGCCCGTCAACGCGGCGGACGCAGCGGCCCTCGAGC

ACGACAAGGCCTACGACCAGCAGCTGCAGGCGGGTGACAATCCGTACCTGCGGTAT

AACCACGCCGACGCCGAGTTTCAGGAGCGTCTGCAAGAAGATACGTCTTTTGGGGG

CAACCTCGGGAGAGCAGTCTTCCAGGCCAAGAAGCGGGTTCTCGAACCTCTCGGTC

TGGTTGAGGAAGGCGCTAAGACGGCTCCTGGAAAGAAGAGACCGGTAGAGCCATC

ACCCCAGCGTTCTCCAGACTCCTCTACGGGCATCGGCAAAAAAGGCCAACAGCCCG

CCAGAAAAAGACTCAATTTTGGCCAGACTGGCGACTCAGAGTCAGTTCCAGACCCT

CAACCTCTCGGAGAACCTCCAGCAGCGCCCTCTGGTGTGGGACCTAATACAATGGC

TGCAGGCGGTGGCGCACCAATGGCAGACAATAACGAAGSCGCCGACGGAGTGGGT

AGTTCCTCGGGAAATTGGCATTGCGATTCCACATGGCTGGGCGACAGAGTCATCAC

CACCAGCACCCGCACCTGGGCCTTGCCCACCTACAATAACCACCTCTACAAGCAAA

TCTCCAGTGCTTCAACGGGGGCCAGCAACGACAACACCTACTTCGGCTACAGCACC

CCCTGGGGGTATTTTGACTTTAACAGATTCCACTGCCACTTTTCACCACGTGACTGG

CAGCGACTCATCAACAACAACTGGGGATTCCGGCCCAAGAGACTCAGCTTCAAGCT

CTTCAACATCCAGGTCAAGGAGGTCACGCAGAATGAAGGCACCAAGACCATCGCCA

ATAACCTCACCAGCACCATCCAGGTGTTTACGGACTCGGAGTACCAGCTGCCGTAC

GTTCTCGGCTCTGCCCACCAGGGCTGCCTGCCTCCGTTCCCGGCGGACGTGTTCATG

ATTCCCCAGTACGGCTACCTAACACTCAACAACGGTAGTCAGGCCGTGGGACGCTC

CTCCTTCTACTGCCTGGAATACTTTCCTTCGCAGATGCTGAGAACGGGCAACAACTT

TGAGTTCAGCTACCAGTTTGAGGACGTGCCTTTTCACAGCAGCTACGCGCACAGCCA

AAGCCTGGACCGGCTGATGAACCCTCTGATTGACCAGTACCTGTACTACTTGTCTCG

GACTCAAACAACAGGAGGCACGGCAAATACGCAGACTCTGGGCTTCAGCCAAGGT

GGGCCTAATACAATGGCCAATCAGGCAAAGAACTGGCTGCCAGGACCCTGTTACCG

CCAACAACGCGTCTCAACGACAACCGGGCAAAACAACAATAGCAACTTTGCCTGGA

CTGCTGGGACCAAATACCATCTGAATGGAAGAAATTCATTGGCTAATCCTGGCATC

GCTATGGCAACACACAAAGACGACGAGGAGCGTTTTTTTCCCAGTAACGGGATCCT

GATTTTTGGCAAACAAAATGCTGCCAGAGACAATGCGGATTACAGCGATGTCATGC

TCACCAGCGAGGAAGAAATCAAAACCACTAACCCTGTGGCTACAGAGGAATACGGT

ATCGTGGCAGATAACTTGCAGCAGCAAAACACGGCTCCTCAAATTGGAACTGTCAA

CAGCCAGGGGGCCTTACCCGGTATGGTCTGGCAGGACAGAGATGTGTACCTTCAGG

GGCCCATCTGGGCAAAGATTCCACACACGGACGGCAACTTCCACCCGTCTCCGCTG

ATGGGCGGCTTTGGCCTGAAACATCCTCCGCCTCAGATCCTGATCAAGAACACGCCT

-continued

```
GTACCTGCGGATCCTCCGACCACCTTCAACCAGTCAAAGTTTGCTTCATTCATCACC

CAATACTCCACAGGACAAGTGAGTGTGGAAATTGAATGGGAGCTGCAGAAAGAAA

ACAGCAAGCGCTGGAATCCCGAAGTGCAGTACACATCCAATTATGCAAAATCTGCC

AACGTTGATTTTACTGTGGACAACAATGGACTTTATACTGAGCCTCGCCCCATTGGC

ACCCGTTACCTTACCCGTCCCCTGTAA
```

SEQ ID NO 3: amino acid sequence of wild-type AAV1 capsid protein

```
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEQSPQEPDSSSGIGKTGQQPAKKR

LNFGQTGDSESVPDPQPLGEPPATPAAVGPTTMASGGGAPMADNNEGADGVGNASGN

WHCDSTWLGDRVITTSTRTWALPTYNNHLYKQISSASTGASNDNHYFGYSTPWGYFDF

NRFHCHFSPRDWQRLINNNWGFRPKRLNFKLFNIQVKEVTTNDGVTTIANNLTSTVQVF

SDSEYQLPYVLGSAHQGCLPPFPADVFMIPQYGYLTLNNGSQAVGRSSFYCLEYFPSQM

LRTGNNFTFSYTFEEVPFHSSYAHSQSLDRLMNPLIDQYLYYLNRTQNQSGSAQNKDLL

FSRGSPAGMSVQPKNWLPGPCYRQQRVSKTKTDNNNSNFTWTGASKYNLNGRESIINP

GTAMASHKDDEDKFFPMSGVMIFGKESAGASNTALDNVMITDEEEIKATNPVATERFG

TVAVNFQSSSTDPATGDVHAMGALPGMVWQDRDVYLQGPIWAKIPHTDGHFHPSPLM

GGFGLKNPPPQILIKNTPVPANPPAEFSATKFASFITQYSTGQVSVEIEWELQKENSKRW

NPEVQYTSNYAKSANVDFTVDNNGLYTEPRPIGTRYLTRPL
```

SEQ ID NO 4: amino acid sequence of wild-type AAV6 capsid protein

```
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPFGLVEEGAKTAPGKKRPVEQSPQEPDSSSGIGKTGQQPAKKRL

NFGQTGDSESVPDPQPLGEPPATPAAVGPTTMASGGGAPMADNNEGADGVGNASGNW

HCDSTWLGDRVITTSTRTWALPTYNNHLYKQISSASTGASNDNHYFGYSTPWGYFDFN

RFHCHFSPRDWQRLINNNWGFRPKRLNFKLFNIQVKEVTTNDGVTTIANNLTSTVQVFS

DSEYQLPYVLGSAHQGCLPPFPADVFMIPQYGYLTLNNGSQAVGRSSFYCLEYFPSQML

RTGNNFTFSYTFEDVPFHSSYAHSQSLDRLMNPLIDQYLYYLNRTQNQSGSAQNKDLLF

SRGSPAGMSVQPKNWLPGPCYRQQRVSKTKTDNNNSNFTWTGASKYNLNGRESIINPG

TAMASHKDDKDKFFPMSGVMIFGKESAGASNTALDNVMITDEEEIKATNPVATERFGT

VAVNLQSSSTDPATGDVHVMGALPGMVWQDRDVYLQGPIWAKIPHTDGHFHPSPLMG

GFGLKHPPPQILIKNTPVPANPPAEFSATKFASFITQYSTGQVSVEIEWELQKENSKRWNP

EVQYTSNYAKSANVDFTVDNNGLYTEPRPIGTRYLTRPL
```

SEQ ID NO 5: amino acid sequence of wild-type AAV8 capsid protein

```
MAADGYLPDWLEDNLSEGIREWWALKPGAPKPKANQQKQDDGRGLVLPGYKYLGPF

NGLDKGEPVNAADAAALEHDKAYDQQLQAGDNPYLRYNHADAEFQERLQEDTSFGG

NLGRAVFQAKKRVLEPLGLVEEGAKTAPGKKRPVEPSPQRSPDSSTGIGKKGQQPARKR

LNFGQTGDSESVPDPQPLGEPPAAPSGVGPNTMAAGGGAPMADNNEGADGVGSSSGN

WHCDSTWLGDRVITTSTRTWALPTYNNHLYKQISNGTSGGATNDNTYFGYSTPWGYF

DFNRFHCHFSPRDWQRLINNNWGFRPKRLSFKLFNIQVKEVTQNEGTKTIANNLTSTIQ
```

-continued

VFTDSEYQLPYVLGSAHQGCLPPFPADVFMIPQYGYLTLNNGSQAVGRSSFYCLEYFPS

QMLRTGNNFQFTYTFEDVPFHSSYAHSQSLDRLMNPLIDQYLYYLSRTQTTGGTANTQT

LGFSQGGPNTMANQAKNWLPGPCYRQQRVSTTTGQNNNSNFAWTAGTKYHLNGRNS

LANPGIAMATHKDDEERFFPSNGILIFGKQNAARDNADYSDVMLTSEEEIKTTNPVATE

EYGIVADNLQQQNTAPQIGTVNSQGALPGMVWQNRDVYLQGPIWAKIPHTDGNFHPSP

LMGGFGLKHPPPQILIKNTPVPADPPTTFNQSKLNSFITQYSTGQVSVEIEWELQKENSKR

WNPEIQYTSNYYKSTSVDFAVNTEGVYSEPRPIGTRYLTRNL

SEQ ID NO 6: amino acid sequence of the AAV-X3_9 capsid protein
MAADGYLPDWLEDNLSEGIREWWALKPGAPKPKANQQKQDDGRGLVLPGYKYLGPF

NGLDKGEPVNAADAAALEHDKAYDQQLQAGDNPYLRYNHADAEFQERLQEDTSFGG

NLGRAVFQAKKRVLEPLGLVEEGAKTAPGKKRPVEQSPQEPDSSSGIGKKGQQPARKR

LNFGQTGDSESVPDPQPLGEPPAAPSGLGPNTMASGGGAPMADNNEGADGVGNSSGN

WHCDSTWLGDRVITTSTRTWALPTYNNHLYKQISNGTSGGSTNDNTYFGYSTPWGYFD

FNRFHCHFSPRDWQRLINNNWGFRPKRLSFKLFNIQVKEVTQNDGVTTIANNLTSTVQV

FSDSEYQLPYVLGSAHQGCLPPFPADVFMIPQYGYLTLNNGSQAVGRSSFYCLEYFPSQ

MLRTGNNFTFSYTFEDVPFHSSYAHSQSLDRLMNPLIDQYLYYLNRTQNQSGSAQNKD

LLFSRGSPAGMSVQPKNWLPGPCYRQQRVSKTKTDNNNSNFTWTGASKYNLNGRESII

NPGTAMASHKDDEDKFFPMSGVMIFGKESAGASNTALDNVMITDEEEIKATNPVATER

FGTVAVNFQSSSTDPATGDVHVMGALPGMVWQDRDVYLQGPIWAKIPHTDGHFHPSP

LMGGFGLKHPPPQILIKNTPVPANPPAEFSATKFASFITQYSTGQVSVEIEWELQKENSKR

WNPEVQYTSNYAKSANVDFTVDNNGLYTEPRPIGTRYLTRPL

SEQ ID NO 7: amino acid sequence of the AAV-X4_10 capsid protein
MAADGYLPDWLEDNLSEGIREWWDLKPGAPKPKANQQKQDDGRGLVLPGYKYLGPF

NGLDKGEPVNAADAAALEHDKAYDQQLQAGDNPYLRYNHADAEFQERLQEDTSFGG

NLGRAVFQAKKRVLEPLGLVEEGAKTAPGKKRPVEPSPQRSPDSSTGIGKKGQQPARKR

LNFGQTGDSESVPDPQPLGEPPAAPSGVGPNTMAAGGGAPMADNNEXADGVGSSSGN

WHCDSTWLGDRVITTSTRTWALPTYNNHLYKQISSASTGASNDNTYFGYSTPWGYFDF

NRFHCHFSPRDWQRLINNNWGFRPKRLSFKLFNIQVKEVTQNEGTKTIANNLTSTIQVFT

DSEYQLPYVLGSAHQGCLPPFPADVFMIPQYGYLTLNNGSQAVGRSSFYCLEYFPSQML

RTGNNFEFSYQFEDVPFHSSYAHSQSLDRLMNPLIDQYLYYLSRTQTTGGTANTQTLGF

SQGGPNTMANQAKNWLPGPCYRQQRVSTTTGQNNNSNFAWTAGTKYHLNGRNSLAN

PGIAMATHKDDEERFFPSNGILIFGKQNAARDNADYSDVMLTSEEEIKTTNPVATEEYGI

VADNLQQQNTAPQIGTVNSQGALPGMVWQDRDVYLQGPIWAKIPHTDGNFHPSPLMG

GFGLKHPPPQILIKNTPVPADPPTTFNQSKFASFITQYSTGQVSVEIEWELQKENSKRWNP

EVQYTSNYAKSANVDFTVDNNGLYTEPRPIGTRYLTRPL

---

What is claimed is:

1. A method for delivering a transgene to a subject, the method comprising administering to the subject an rAAV comprising an isolated AAV capsid protein comprising the amino acid sequence set forth in SEQ ID NOs: 6 or 7, wherein the transgene comprises skeletal muscle-specific promoter.

2. The method of claim 1, wherein the transgene is delivered to muscle tissue of the subject.

3. The method of claim 1, wherein the transgene comprises a protein-coding gene.

4. The method of claim 3, wherein the protein-coding gene is a therapeutic protein or a secreted protein.

5. The method of claim 3, wherein the protein-coding gene is a minigene encoding minidystrophin, miniutrophin, or minidysferlin.

6. The method of claim 1, wherein the transgene encodes a small interfering nucleic acid.

7. The method of claim 6, wherein the small interfering nucleic acid is a miRNA or artificial miRNA (amiRNA).

8. The method of claim 2, wherein the transgene encodes a miRNA sponge that inhibits the activity of at least one miRNA in the subject or animal.

9. The method of claim 8, wherein the miRNA is expressed in a cell of the muscle tissue.

10. The method of claim 9, wherein the muscle tissue is skeletal muscle.

11. The method of claim 1, wherein the promoter is human skeletal actin (HSA) or alpha skeletal actin (ACTA1), muscle creatine kinase (MCK), any one of promoters CK1 to CK7, or MHCK7.

* * * * *